United States Patent
Delmarre et al.

(10) Patent No.: US 9,333,177 B2
(45) Date of Patent: May 10, 2016

(54) DELIVERY CARRIER

(75) Inventors: David Delmarre, Illkirch Graffenstaden (FR); Marie-Sophie Lina Martina, Illkirch Graffenstaden (FR); Jan Emiel Godelieve Vertommen, Bornem (BE)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 13/508,790

(22) PCT Filed: Oct. 26, 2010

(86) PCT No.: PCT/IB2010/054844
§ 371 (c)(1),
(2), (4) Date: May 9, 2012

(87) PCT Pub. No.: WO2011/055269
PCT Pub. Date: May 12, 2011

(65) Prior Publication Data
US 2012/0308655 A1    Dec. 6, 2012

Related U.S. Application Data

(60) Provisional application No. 61/259,355, filed on Nov. 9, 2009, provisional application No. 61/377,528, filed on Aug. 27, 2010.

(51) Int. Cl.
*A61K 9/48* (2006.01)
*A61K 9/127* (2006.01)
*A61K 31/451* (2006.01)
*A61K 47/14* (2006.01)
*A61K 47/44* (2006.01)

(52) U.S. Cl.
CPC ............. *A61K 9/4858* (2013.01); *A61K 31/451* (2013.01); *A61K 47/14* (2013.01); *A61K 47/44* (2013.01)

(58) Field of Classification Search
CPC ....... A61K 47/44; A61K 9/48; A61K 9/4841; A61K 9/1075; A61K 8/14
See application file for complete search history.

(56) References Cited

U.S. PATENT DOCUMENTS

| | | | |
|---|---|---|---|
| 5,919,481 A | 7/1999 | Cody et al. | |
| 6,294,192 B1 | 9/2001 | Patel et al. | |
| 6,309,663 B1 | 10/2001 | Patel et al. | |
| 6,451,339 B2 | 9/2002 | Patel et al. | |
| 2003/0104048 A1 | 6/2003 | Patel et al. | |
| 2004/0052845 A1* | 3/2004 | Appel et al. | 424/471 |
| 2005/0191343 A1* | 9/2005 | Liang | 424/450 |
| 2006/0160888 A1* | 7/2006 | Kottayil et al. | 514/454 |
| 2006/0188561 A1 | 8/2006 | Bhalani et al. | |
| 2006/0275358 A1* | 12/2006 | Lin | 424/451 |
| 2007/0082016 A1* | 4/2007 | Ottinger | 424/400 |
| 2008/0234380 A1* | 9/2008 | Shapiro | 514/565 |
| 2008/0317844 A1* | 12/2008 | Dudley et al. | 424/456 |

FOREIGN PATENT DOCUMENTS

| | | |
|---|---|---|
| EP | 0 815 854 A1 | 1/1998 |
| WO | WO 97/21440 | 6/1997 |
| WO | WO 97/40823 | 11/1997 |
| WO | WO 9740823 A1 * | 11/1997 |
| WO | WO 98/40051 | 9/1998 |

OTHER PUBLICATIONS

Papich, "Pharmacologic Consideration for Opiate Analgesic and Nonsteroidal Anti-Inflammatory Drugs", Management of Pain, vol. 30, No. 4, 815-837, Jul. 2000.*
Schiller, "Chronic Diarrhea", Current Treatment Options in Gastroenterology, 8:259-266, 2005.*
Taha, "Development and Characterization of New Indomethacin Self-Nanoemulsifying Formulations", Scientia Pharmaceutica, 77, 443-451, Mar. 14, 2009.*
Cadé, D. et al., "Liquid Filling in Hard Gelatin Capsules—Preliminary Steps", Capsugel R&D, 68000 Colmar, France, B.T. Gattefossé, No. 89, 1996, pp. 15-19.
Cole, Ewart T. "Liquid filled and sealed hard gelatin capsules", Capsugel Division, Warner-Lambert Co., Capsugel Library, originally published in Gattefossé Bulletin nr 92, 1999, pp. 3-12.
International Search Report from International Application No. PCT/IB2010/054844 mailed Feb. 1, 2011.

* cited by examiner

*Primary Examiner* — Robert T Crow
*Assistant Examiner* — John P Nguyen
(74) *Attorney, Agent, or Firm* — Klarquist Sparkman, LLP

(57) ABSTRACT

The present invention relates to a novel liquid delivery carrier comprising a specific grade of glyceryl caprylate and PEG-40 hydrogenated castor oil in particular amounts. This carrier can be loaded with slightly or poorly water soluble substances and filled into hard gelatin capsule shells for final administration to a subject. Also disclosed are filling compositions comprising such delivery carrier and hard gelatin capsules filled with the carrier and the composition of the invention. The delivery carrier of the invention proved to be compatible with both the hard gelatin capsule shells and the substances loaded into it.

2 Claims, 2 Drawing Sheets

DELIVERY CARRIER

Figure 1:
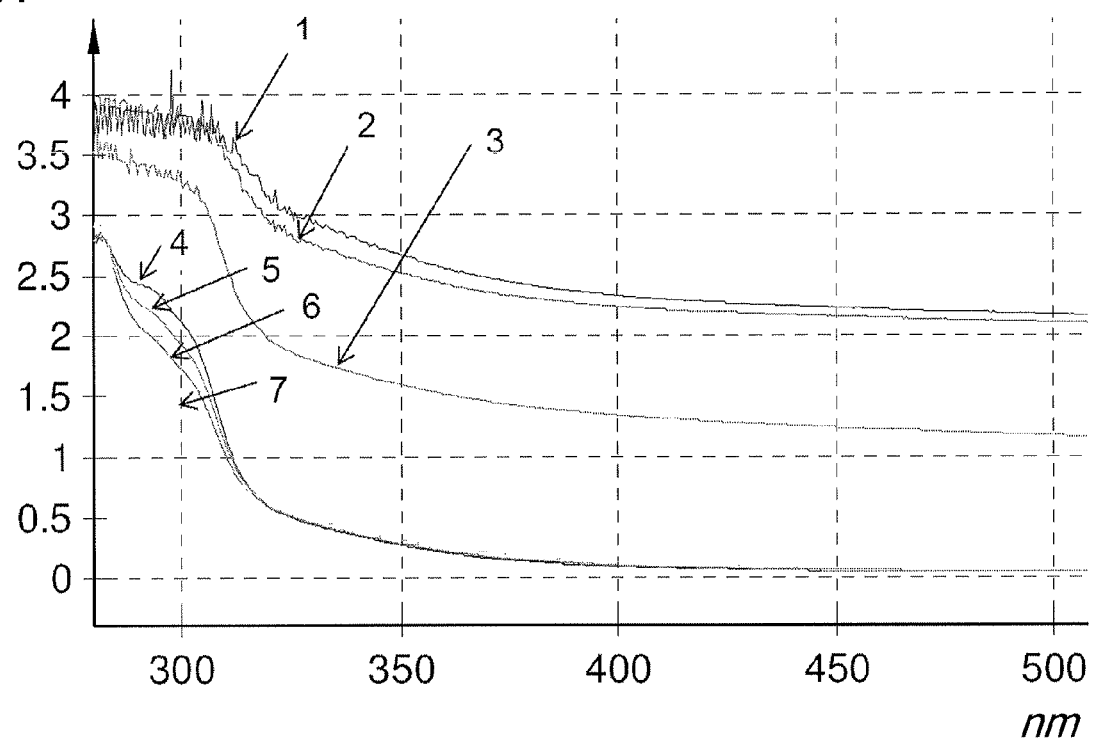

This application is a national stage entry under 35 U.S.C. §371 of International Application No. PCT/IB2010/054844 filed on Oct. 26, 2010, which claims priority of U.S. Provisional Application No. 61/259,355 filed on Nov. 9, 2009, and U.S. Provisional Application No. 61/377,528 filed on Aug. 27, 2010, all of which are incorporated herein by reference.

FIELD OF THE INVENTION

The present invention relates to a new liquid delivery carrier suitable for filling into hard gelatin capsules, a process for its manufacture, its use to deliver active substances to humans or animals via hard capsules and a hard capsule filled with such carrier.

BACKGROUND OF THE INVENTION

Capsules are widely used in the pharmaceutical field as oral dosage forms for administration to humans and animals of e.g. pharmaceuticals, veterinary products, food and dietary supplements. Advantages of capsules over other conventional forms may include better patient compliance, greater flexibility in dosage form design and less expensive manufacturing process. Pharmaceutical capsules are conventionally divided into soft shell capsules (hereinafter soft capsules) and hard shell capsules (hereinafter hard capsules). The characteristics of soft and hard capsules are well known to any skilled person working in the pharmaceutical field.

For many pharmaceutical applications, e.g. when slightly or poorly water soluble substances are to be administered, it is often desirable that the substances to be encapsulated are pre-mixed with a suitable delivery carrier to form a composition which is then filled into capsules. For this reason, it is desirable that such delivery carrier be compatible with capsule shell in the sense that it must not affect capsule shell stability after filling. Typical compatibility issues that may arise are impairment of the mechanical properties of the capsule shells resulting e.g. in leaks and/or softening of the shells and/or impairment of the chemical properties of the capsule shells such as modification of shell dissolution profile.

It is known that hard capsules are often commercially preferable over soft capsules since they have a simpler manufacturing process e.g. in terms of less expertise that is generally required to operate the process, more flexibility in filling step, easier equipment operability. For these reasons, it would be desirable that a delivery carrier be compatible with hard capsules.

It is also desirable that the delivery carrier be not visually opaque or milky since this has been linked to lower patient compliance.

It is also desirable that the delivery carrier be liquid since this facilitates capsule filling step as well as gastro-intestinal release and absorption of the substance(s) after capsule shell disintegration.

It is also desirable that the liquid delivery carrier be compatible with the substances intended to be pre-mixed with it. Typically, instability can result in oxidation, hydrolysis for example over time of the substances mixed with the carrier.

U.S. Pat. No. 6,294,192, EP1158959A, EP1210063A and U.S. Pat. No. 6,451,339 disclose compositions comprising a liquid carrier for the administration of hydrophilic or hydrophobic active agents. Generally, the carriers are comprised of one hydrophilic surfactant and one hydrophobic surfactant, the former being in greater amount. These documents disclose huge lists of ingredients that can be variably combined to obtain equally effective carriers. No data are provided to infer stability of hard capsule shells after filling with such carriers.

E. T. Cole, "Liquid filled and sealed hard gelatin capsules," Gattefossé Bulletin nr. 92 (1999), describes the use of hard gelatin capsules as an alternative for liquid/semi-solid formulations. Results from a screening program are presented based on which a list of functional excipients which are compatible with the gelatin shell is drawn up. When MCM (medium chain monoglycerides) ingredients are discussed, a suggestion is made that glycerol levels below 5% be adopted. Capmul MCM is listed in a multi-ingredient list comprising excipients incompatible with hard gelatin shells that are globally said to be usable only if admixed with compatible excipients. No suggestions are made to select a specific Capmul MCM grade nor clarifications are provided as to how Capmul MCM grade selection, its amount and the presence of further excipient would impact pharmaceutically important properties of the formulations such as transparency or viscosity.

U.S. Pat. No. 5,919,481 discloses carriers for the administration of substances (including hydrophobic ones) prone to human abuse. The aim of these carriers is to reduce the risk of drug abuse. Accordingly, these carriers must be highly viscous at room temperature so that they cannot be freely removed with a syringe. Additionally, no data are provided to infer stability of hard capsule shells in case these carriers had to be filled into hard capsules.

Thus, an object of the present invention is to provide a liquid delivery carrier that is compatible with hard capsule shells. Further objects are to provide a delivery carrier that is clear at room temperature and that is to a large extent compatible with the substances that are mixed with it before being filled into hard capsule shells.

SUMMARY OF THE INVENTION

The above and other objects are achieved by a liquid delivery carrier comprising:
  a glyceryl caprylate containing 3% or less w/w of free glycerol, in an amount between 40% and 90% by weight of the weight of the carrier, lower limit excluded, and
  PEG-40 hydrogenated castor oil in an amount between 10% and 60% by weight of the weight of the carrier, upper limit excluded.

The above and other objects are also achieved by a composition particularly suitable for filling into hard gelatin capsules, said composition comprising a delivery carrier as defined above and one or more additional substances.

The above and other objects are also achieved by a hard gelatin capsule filled with a delivery carrier as defined above or a composition as defined above.

The above and other objects are also achieved by the process for manufacturing a hard gelatin capsule, said method comprising the step of filling a hard gelatin capsule shell with a delivery carrier as defined above or a composition as defined above.

The above and other objects are also achieved by the use of a delivery carrier as defined above for the administration of one or more substances to a human or an animal.

FIGURES

FIG. 1 is an enlargement of UV-visible absorbance curve at 25° C. of seven different carriers obtained by mixing a glyceryl caprylate containing 3% or less w/w of free glycerol as defined above and a PEG-40 hydrogenated castor oil. Y axis represents Absorbance values (A) expressed in arbitrary units, whereas X axis represents wavelength (λ) calculated in nm. In FIG. 1:

sample 1=Capmul® MCM C8 to Cremophor® RH40=10/90—comparative
sample 2=Capmul® MCM C8 to Cremophor® RH40=20/80—comparative
sample 3=Capmul® MCM C8 to Cremophor® RH40=30/70—comparative
sample 4=Capmul® MCM C8 to Cremophor® RH40=40/60—comparative
sample 5=Capmul® MCM C8 to Cremophor® RH40=50/50
sample 6=Capmul® MCM C8 to Cremophor® RH40=60/40
sample 7=Capmul® MCM C8 to Cremophor® RH40=80/20.

Figure 2:
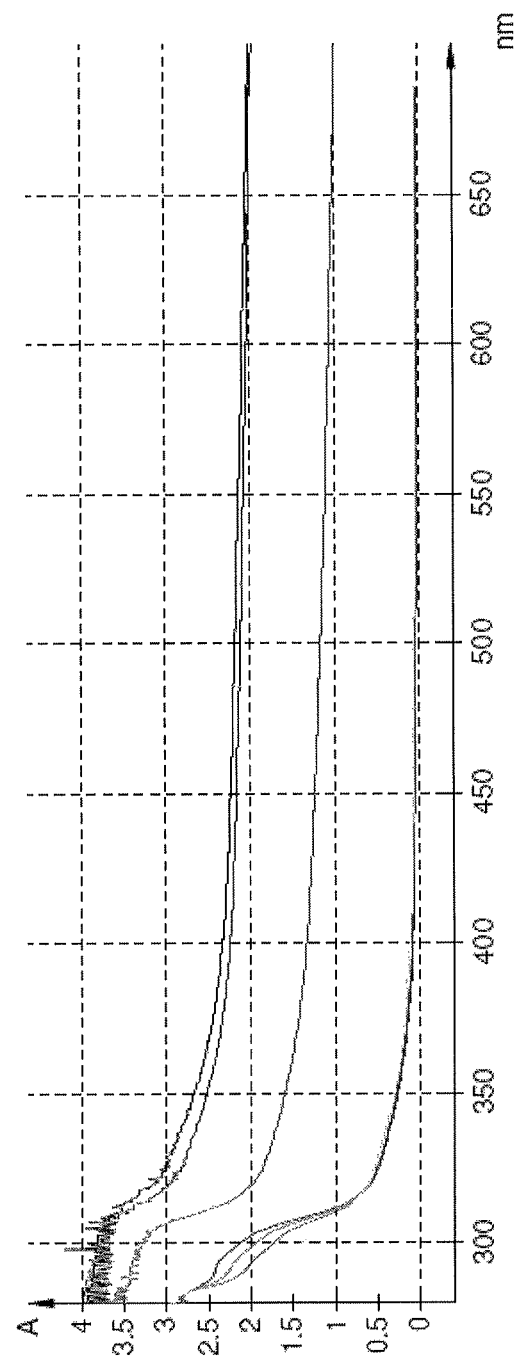

FIG. 2 is the complete UV-visible absorbance curve of the same samples of FIG. 1.

DETAILED DESCRIPTION OF THE INVENTION

Unless otherwise indicated, in the current invention hard capsules are commercially available, conventional hard capsules intended for oral administration to a human or animal being. The hard capsules of the invention are generally manufactured by using a dip molding process and equipment. In this process, pin molds are dipped into an aqueous-based film forming composition. By subsequently gelling the composition adhered on the pins a film is formed. The film is then dried, stripped off the pins and cut to a desired length. Thus, capsules caps and bodies are obtained. Such two parts are then co-axially, telescopically joined so as to form a capsule shell. Normally, caps and bodies have a side wall, an open end and a closed end. The length of the side wall of each of said parts is generally greater than the capsule diameter. The capsule caps and bodies are telescopically joined together so as to make their side walls partially overlap and obtain a hard capsule shell. "Partially overlap" also encompasses an embodiment wherein the side walls of caps and bodies have substantially the same length so that, when a cap and a body are telescopically joined, the side wall of said cap encases the entire side wall of said body. Unless otherwise indicated, "capsule" refers to filled capsule shells whereas "shell" specifically refers to an empty capsule. Since the hard capsule shells of the invention are filled with substances in liquid form, it is intended that if desired the hard capsules of the invention may be sealed or banded according to conventional techniques.

Unless otherwise indicated, the hard capsules and shells of the invention are gelatin hard capsules and shells. This means that these shells are typically obtained by dip molding process from a water solution containing gelatin as shell film forming polymer and other optional ingredients known to skilled persons.

Unless otherwise indicated, in the present invention references to compatibility of the carrier with hard capsule shells, or stability of a hard capsule shell, preferably means that the carrier of the invention, after filling into a hard capsule shell as defined above, does not impact at least mechanical stability of said shell, more preferably both mechanical and chemical stability of said shell. Mechanical stability can for example be evaluated based on maintenance of hardness of the shell and absence of leaks whereas chemical stability can for example be evaluated based on maintenance of an appropriate dissolution profile of an encapsulated substance (for this latter aspect, reference can be made to e.g. USP-32 substance monographs).

In one embodiment, the carrier of the invention, after filling into a hard capsule shell as defined above, does not impact mechanical and chemical stability, beyond an acceptable level. In one embodiment, an acceptable level is a commercially acceptable level. In one embodiment, a commercially acceptable level is a level recognised by a skilled person in the field of hard capsules, preferably liquid filled hard capsules, as a satisfactory level to commercialize the carrier filled hard capsules with acceptable manufacturing costs.

In one embodiment, a carrier does not affect mechanical stability of a hard capsule shell as defined above beyond an acceptable level if, when filling a batch of preferably at least 50 hard capsule shells with said carrier and subjecting the filled shells to a mechanical robustness test (e.g. tube test) at a specified shell loss on drying (LOD), less than 50% of the capsules in said batch breaks at about 8% of shell water content, less than 30% of capsules in said batch breaks at about 10% of shell water content and less than 5% of capsules breaks at a shell water content comprised between about 13% and 16%.

Such "Mechanical robustness test", demonstrates alterations in the mechanical properties of the capsule due to interactions between the fill and the shell and to evaluate the potential tendency for brittleness when filled and stored at various relative humidity conditions.

In one embodiment, the method to test Mechanical robustness is performed as disclosed in D. Cadé and N. Madit, "Liquid Filling in Hard Gelatin Capsules—Preliminary Steps", Bulletin Technique Gattefossé, 1996.

In one embodiment, a carrier does not affect chemical stability of a hard capsule shell as defined above beyond an acceptable level if, when filling a batch of preferably at least 6 hard capsule shells with said carrier and acetaminophen, none of the filled capsules in said batch release less than about 80% of the filled acetaminophen at 45 minutes in simulated gastric fluid (pepsin) after 6 months at storage conditions of 40° C. and 75% RH. Acetaminophen dissolution is evaluated in accordance with, and using equipment and method conditions disclosed in USP-32 for Acetaminophen.

Such "Dissolution test", using an immediate release reference (i.e. acetaminophen), indicates changes in the capsule dissolution rate due to gelatin cross-linking reaction that may occur as a consequence of interactions between the filling and the shell.

In one embodiment, the method to test dissolution properties is performed as disclosed in D. Cadé and N. Madit, "Liquid Filling in Hard Gelatin Capsules—Preliminary Steps", Bulletin Technique Gattefossé, 1996.

In a first aspect, the present invention relates to a delivery carrier as defined above.

The glyceryl caprylate of the invention is commercially available. A typical example is Capmul® MCM C8. Chemically, Capmul® MCM C8 is obtained by direct esterification of glycerol mainly with caprylic acid and is mainly composed of glyceryl monoesters and diesters. Capmul® MCM C8 is technically distinguished over other existing glyceryl caprylates like Capmul® MCM L8 and Imwitor® 308 mainly in light of the amount of free glycerol although differences in terms of glyceryl substitution pattern (type and amounts of esterifying fatty acids) are also present. In fact, Capmul® MCM C8 has maximum amount of free glycerol of 3% w/w, whereas Capmul® MCM L8 has a maximum amount of free glycerol of 7% w/w and Imwitor® 308 has a maximum amount of free glycerol of 6% w/w.

As it is shown in the examples of this application, Capmul® MCM L8 and Imwitor® 308 were found unsuitable to reach an acceptable stability with gelatin hard capsule shells.

Accordingly, in one embodiment of the invention, a glyceryl caprylate containing 3% or less w/w of free glycerol is the only glyceryl caprylate present in the carrier.

However, though not being preferred, mixtures of a glyceryl caprylate containing 3% or less w/w of free glycerol (e.g. Capmul® MCM C8) with glyceryl caprylates grades having different amount of free glycerol (e.g. Capmul® MCM L8 and/or Imwitor® 308) are also possible provided that the total amount of free glycerol in the carrier is less than about 3.2% w/w of the carrier, typically less than about 2.7% w/w of the carrier, for example comprised between about 1.5% and about 2.7% w/w of the carrier.

In one embodiment of the invention, a glyceryl caprylate containing 3% or less w/w of free glycerol is the only free glycerol-containing ingredient present in the carrier.

However, though not being preferred, mixtures of a glyceryl caprylate containing 3% or less w/w of free glycerol (e.g. Capmul® MCM C8) with other optional ingredients containing free glycerol are also possible provided that the total amount of free glycerol in the carrier is less than about 3.2% w/w of the carrier, typically less than about 2.7% w/w of the carrier, for example comprised between about 1.5% and about 2.7% w/w of the carrier The PEG-40 hydrogenated castor oil of the invention is commercially available. A typical example is Cremophor® RH40, also known as Polyoxyl 40 Hydrogenated Castor Oil or PEG-40 Hydrogenated Castor Oil.

In one embodiment, the glyceryl caprylate containing 3% or less w/w of free glycerol as defined above is present in an amount between 50% and 90%, preferably between 50% and 80%, more preferably between 60% and 80%, more preferably between 70% and 80%, even more preferably at 75% by weight of the weight of the carrier. Amounts of glyceryl caprylate higher than 90% by weight of the weight of the carrier are thought to lead to incompatibility with hard capsule shells, e.g. an unsuitable capsule shell dissolution profile and/or softening of the capsules. Amounts of glyceryl caprylate higher than 40% by weight of the weight of the carrier are preferred since they allow a better transparency and a lower viscosity of the carrier.

In one embodiment, the PEG-40 hydrogenated castor oil is present in an amount between 50% and 10%, preferably between 50% and 20%, more preferably between 40% and 20%, more preferably between 30% and 20%, even more preferably at 25% by weight of the weight of the carrier.

In a preferred embodiment, the carrier comprises the glyceryl caprylate containing 3% or less w/w of free glycerol as defined above in an amount between 50% and 80% and the PEG-40 hydrogenated castor oil in an amount between 50% and 20% by weight of the weight of the carrier; preferably the glyceryl caprylate as defined above in an amount between 70% and 80% and the PEG-40 hydrogenated castor oil in an amount between 30% and 20% by weight of the weight of the carrier; more preferably the glyceryl caprylate as defined above in an amount of 75% and the PEG-40 hydrogenated castor oil in an amount of 25% by weight of the weight of the carrier.

In a preferred embodiment, the carrier of the invention consists of glyceryl caprylate containing 3% or less w/w of free glycerol as defined above and PEG-40 hydrogenated castor oil, in any of the amounts indicated above.

In a preferred embodiment, the pure (i.e. non diluted) carrier of the invention has an UV absorbance at 400 nm and 25° C. of less than 1 but higher than 0, preferably less than 0.5, more preferably less than 0.25. In this preferred embodiments, the carrier has been found to be clear at a simple visual inspection at 25° C.

Unless otherwise indicated, in the present invention room temperature is preferably 25° C.

The delivery carrier of the invention is liquid at room temperature. Unless otherwise indicated, "liquid" means having a viscosity at 25° C. less than the viscosity of a carrier consisting of 100% w/w of PEG-40 hydrogenated castor oil. In one embodiment, the carrier of the invention has a viscosity of less than 2 Pa·s, preferably less than 400 mPa·s but higher than 0, more preferably between 100 and 400 mPa·s, more preferably between 100 and 300 mPa·s, even more preferably between 100 and 200 mPa·s at 25° C. Viscosity of the carrier can be measured according to any suitable equipment known in the field, such as a viscosimeter or a rheometer (for example Mars II from Haake). In this preferred liquid embodiments, the carrier is advantageous as e.g. a lower viscosity makes capsule shells filling easier and substance release after administration prompter.

The delivery carrier of the invention can be easily prepared by simply mixing the ingredients in the desired amounts into appropriate pharmaceutical mixing equipment for fluids and semi-solids.

In another aspect, the present invention relates to a composition particularly for filling into hard gelatin capsules, said composition comprising a delivery carrier as defined above and one or more additional substances. Hereinafter, the composition of the invention is also referred to as "filling composition".

In one embodiment, the additional substances to be mixed with the carrier are hydrophobic or lipophilic substances. In one embodiment, hydrophobic substances are substances that tend to associate in an aqueous environment due to presence of non-polar groups in their structure. In one embodiment, lipophilic substances are substances that dissolve in non-polar $C_{4-28}$ hydrocarbon solvents. In one embodiment, hydrophobic or lipophilic substances sparingly, slightly, very slightly water soluble or water insoluble substances as defined in USP 32-NF 27. In one embodiment, hydrophobic or lipophilic substances have a water solubility of 1 mg/ml or less, preferably between 0 and 1 mg/ml, upper limit included. In one embodiment, hydrophobic or lipophilic substances have a Log P (octanol/water) of above 2. Preferably, additional substances that can be formulated into the carrier of the invention are pharmaceutically active substances. A preferred example of pharmaceutically active substance that can be formulated in the carrier of the invention is loperamide hydrochloride.

Additional substances can be mixed with the carrier of the invention in any desired amount since compositions can be filled into hard capsules both in the form of a solution or a suspension. In the preferred embodiment wherein the one or more additional substances are pharmaceutically active substances, preferred amounts to be mixed with the carrier are pharmacologically effective amounts. Typically, loperamide hydrochloride can be used in an amount of 10 mg per gram of the filling composition. In a preferred embodiment, the one or more additional substances are mixed with the carrier so as to obtain a solution. A skilled person can readily determine by means of routine tests (e.g. spectrophotometry or empirical visual observation) when solutions are obtained. Typically, a solution is obtained when UV-visible absorbance of the composition at 400 nm and 25° C. is within the values provided above for the carrier.

Optionally, the filling composition of the invention can further contain other ingredients such as antioxidants, preservatives and colorants. Typical examples of preservative are BHA (butyl hydroxyanisole), BHT (butyl hydroxutoluene), and ascorbyl palmitate. Antioxidants can be used in any amount readily determinable by any skilled person inter alia depending on the nature of the substances to be included in the carrier. Typically, BHA can be used in an amount between 0.1 and 0.4 mg/g of filling composition, preferably at 0.2 mg/g of filling composition.

The filling composition of the invention can be easily prepared by simply mixing the ingredients in desired amounts into appropriate pharmaceutical mixing equipment for fluids and semi-solids.

In another aspect, the present invention relates to a hard gelatin capsule filled with a delivery carrier as defined above or a composition as defined above.

In a preferred embodiment, the filled hard gelatin capsule of the invention is made tamper-proof by using appropriate techniques to make the joint permanent. Typically, sealing or banding techniques can be used where these techniques are well-known to any skilled person in the field of hard capsules.

In another aspect, the present invention relates to a process for manufacturing a hard gelatin capsule as defined above, said method comprising the step of filling a hard gelatin capsule shell with a delivery carrier as defined above or a composition as defined above.

In a preferred embodiment, the process of the invention comprises a further step of making the filled hard gelatin capsule shell tamper-proof, said step being performed after the step of filling said shell. In a preferred embodiment, the step of making the shell tamper-proof comprises sealing or banding the filled hard gelatin capsule shell.

In another aspect, the present invention relates to the use of a delivery carrier as defined above for the administration of one or more substances to a human or an animal. Substances to be administered are preferably as defined above in connection with the filling composition of the invention.

Further embodiments and advantages of the present invention will become apparent to a skilled reader in light of the examples provided below.

Example 1

Three different delivery carriers where prepared by mixing the following ingredients (amounts are referred to grams of the final delivery carrier):
[A] 750 mg/g Capmul® MCM C8 and 250 mg/g Cremophor® RH40;
[B] 750 mg/g Capmul® MCM L8 and 250 mg/g Cremophor® RH40; and
[C] 750 mg/g Imwitor® 308 and 250 mg/g Cremophor® RH40.
Each of the three delivery carriers was filled in hard gelatin capsule (Licaps®, from Capsugel). Capsules were placed in different environmental conditions (2.5, 10, 30, 50 and 65% RH) at room temperature and after three weeks storage, the number of broken capsules was assessed using a tube-test. The loss on drying (LOD) was measured and the percentage of broken capsules was calculated for a 10% LOD. The results are reported in Table 1 below.

Dissolution testing was performed after 3 weeks, 3 months and 6 months storage at 40° C./75% RH. The capsules were emptied, cleaned and filled with an immediate release reference (acetaminophen). Dissolution tests were performed according to the acetaminophen USP monograph using a type 2 apparatus at 50 rpm. The results are reported in Table 1 below.

TABLE 1

| Delivery carrier | % Broken capsules after 3 weeks at 10% LOD | % Acetaminophen dissolved at 45 minutes |
|---|---|---|
| A | 12% | 81.8% in water (after 6 months) |
| B | 28% | Capsule too soft to be tested after 6 months |
| C | 10% | 69.9% in SGF (after 6 months) |

SGF = simulated gastric fluid (pepsin)

The delivery carrier [A] did not impact either the mechanical performance of the shell (as % of broken capsules was within an acceptable range, <20%) or its chemical characteristics as evidenced by an acceptable dissolution profile after 6 months of storage (>80% dissolved at 45 min). By contrast, the delivery carrier [B] led to a higher percentage of broken capsules and, above all, the dissolution test could not be performed at 6 months due to a softening of the hard shell. Finally, delivery carrier [C] clearly impacted the chemical properties of the shell leading to an improper shell dissolution profile and low acetaminophen release even in a SGF media.

Example 2

A filling composition [D] was prepared by mixing the following ingredients (amounts are referred to grams of the final filling composition):
10 mg/g loperamide HCl
0.2 mg/g Butyl hydroxyanisole (BHA)
742.4 mg/g Capmul® MCM C8
247.4 mg/g Cremophor® RH40
The composition was filled into a size 1 hard gelatin capsule shell (Licaps®, from Capsugel). The same parameters discussed in Example 1 were tested for the capsule of example 2. The results are reported in Table 2 below.

TABLE 2

| | % Broken capsules after 3 weeks at 10% LOD | % Loperamide dissolved at 45 minutes |
|---|---|---|
| D | 16% | 98.9% in SGF (after 6 months) |

Results supported an acceptable maintenance of mechanical and chemical properties of the shell.

Example 3

The visual aspect of the same seven carriers tested for UV-visible absorbance in FIGS. 1 and 2 was evaluated and reported in Table 3.

TABLE 3

| | Sample 1 | Sample 2 | Sample 3 | Sample 4 | Sample 5 | Sample 6 | Sample 7 |
|---|---|---|---|---|---|---|---|
| Visual aspect | -- | -- | - | + | + | ++ | ++ |

+ = clear;
- = opaque

Samples 1 and 2 (higher % w/w of Cremophor® RH40) were milky, sample 3 was opaque, whereas samples 4 and 5 were clear and samples 6 and 7 (higher % w/w of Capmul® MCM C8) were very clear, perfectly transparent.

Example 4

The viscosity of the same seven carriers tested for UV absorbance in FIGS. 1 and 2 was evaluated at 20° C. and 25° C. using a conventional rheometer. Results are reported in Table 4.

| Excipient | F1 | F2 | F3 | F4 | F5 | F6 | F7 | F8 | F9 | F10 | F11 | F12 |
|---|---|---|---|---|---|---|---|---|---|---|---|---|
| Cremophor ® RH40 (BASF) | 100 | | 25 | 25 | 25 | 10 | 50 | 25 | 25 | 20 | 60 | |
| Capmul ® MCM C8 (Abitec) | | 100 | 75 | | | 90 | 50 | 50 | 25 | 80 | 40 | |
| Capmul ® MCM L8 (Abitec) | | | | 75 | | | | | 25 | 50 | | |
| Imwitor ® 308 (Sasol) | | | | | 75 | | | | | | | 100 |
| Total | 100 | 100 | 100 | 100 | 100 | 100 | 100 | 100 | 100 | 100 | 100 | 100 |

TABLE 4

Measurement of viscosity (Pa · s) for combination of
Capmul ® MCM C8/Cremophor ® RH40 at different ratios

| Weight ratio Capmul ® MCM C8/Cremophor ® RH40 | 20° C. | 25° C. |
|---|---|---|
| 10/90 | 2.812 | 1.648 |
| 20/80 | 1.541 | 0.922 |
| 30/70 | 1.021 | 0.579 |
| 40/60 | 0.692 | 0.417 |
| 50/50 | 0.358 | 0.259 |
| 60/40 | 0.291 | 0.210 |
| 80/20 | 0.186 | 0.135 |

Results show that within the range limits indicated for the present invention, higher amounts of Capmul® MCM C8 are preferred as they lead to carriers endowed with a better viscosity.

Example 5

This example discusses the mechanical and chemical shell compatibility of mixture of different grades of commercial glyceryl caprylate and Cremophor® RH40 with the Licaps® technology from Capsugel France. Different grades of glyceryl caprylate from different suppliers are available on the market. The main difference between the different grades of glyceryl caprylate is the percentage of free glycerol.

The objective is to assess the potential for interactions between capsule shells and fillings by deliberately exposing capsules filled with different carriers but without a packaging barrier directly to environmental conditions which are outside normal using conditions. For example, loss on drying values of about 8% and 10% where adopted instead of the conventional and recommended 13% to 16% LOD. Similarly, accelerated storage conditions (40° C./75% RH) were adopted.

Materials: Capsugel evaluated the compatibility mixture of Cremophor® RH40 provided by BASF and glyceryl caprylate from Abitec and Sasol. Two different grades from Abitec were evaluated (Capmul® MCM C8 and Capmul® MCM L8). The compatibility study was initiated in transparent size 1 Licaps® supplied by Capsugel (same batch number of Licaps®) except for the formulation F1 which was initiated in size 0 Licaps®.

The following table summarized the different compositions (F1 to F12) of the carriers tested (values expressed as % by weight over total weight of the carrier)

Methods:

Compatibility testing involved evaluation of the following aspects in a batch of about 350 hard gelatin capsules:

- the "Mechanical robustness test", which demonstrates alterations in the mechanical properties of the capsule due to interactions between the fill and the shell and to evaluate the potential tendency for brittleness when filled and stored at various relative humidity conditions; and
- the "Dissolution test", using an immediate release reference (i.e. acetaminophen) in demineralised water or simulated gastric fluid (pepsin), indicates changes in the capsule dissolution rate due to gelatin cross-linking reaction that may occur as a consequence of interactions between the fill and the shell.

Stability results were classified in the following manner:

Mechanical resistance test: less than 50% of filled capsules broke at 8% of shell water content (LOD), less than 30% of capsules broke at 10% of shell water content (LOD) and less than 5% of capsules broke for shell water content between 13% and 16%.

+=the carrier allowed meeting the specifications above

−=the carrier did not allow meeting the specifications above;

Dissolution profile (USP32 Acetaminophen monograph specification): in simulated gastric fluid (pepsin) not less than 80% of acetaminophen dissolved at 45 minutes +=all filled capsules met the specifications above after 6 months in accelerated storage conditions −=one or more filled capsules did not meet the specifications above at 6 months in accelerated storage conditions

|  | F1 | F2 | F3 | F4 | F5 | F6 | F7 | F8 | F9 | F10 | F11 | F12 |
|---|---|---|---|---|---|---|---|---|---|---|---|---|
| Mechanical robustness | + | + | + | − | − | + | + | − | − | + | + | − |
| Dissolution | − | − | + | − | − | + | + | + | + | + | − | + |

The invention claimed is:

1. A liquid delivery carrier consisting of a glyceryl caprylate containing 3% or less w/w of free glycerol, in an amount ranging from about 70% to about 80% by weight of the weight of the carrier, and PEG-40 hydrogenated castor oil in an amount ranging from about 20% to about 30% by weight of the weight of the carrier, wherein the carrier at 25° C. has an UV absorbance of less than about 1 at 400 nm and a viscosity ranging from about 100 to about 200 mPa·s.

2. The carrier according to claim 1, wherein the glyceryl caprylate is in an amount of about 75% by weight of the weight of the carrier and the PEG-40 hydrogenated castor oil is in an amount of about 25% by weight of the weight of the carrier.

* * * * *